US00PP30565P3

(12) United States Plant Patent
Bivin

(10) Patent No.: US PP30,565 P3
(45) Date of Patent: Jun. 11, 2019

(54) ***HYDRANGEA* PLANT NAMED 'BIV01'**

(50) Latin Name: *Hydrangea quercifolia*
Varietal Denomination: BIV01

(71) Applicant: Tara Bivin, Ranburne, AL (US)

(72) Inventor: Tara Bivin, Ranburne, AL (US)

(73) Assignee: Plant Development Services, Inc., Loxley, AL (US)

( * ) Notice: Subject to any disclaimer, the term of this patent is extended or adjusted under 35 U.S.C. 154(b) by 0 days.

(21) Appl. No.: 15/732,162

(22) Filed: Sep. 26, 2017

(65) Prior Publication Data

US 2019/0098816 P1 Mar. 28, 2019

(51) Int. Cl.
*A01H 5/02* (2018.01)

(52) U.S. Cl.
USPC ..... Plt./250

(58) Field of Classification Search
USPC ..... Plt./226, 250
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Hydrangea* cultivar named 'BIV01' is disclosed, characterized by a an exceptionally dense inflorescence with tightly held individual flowers forming a spongey texture. Plants can be grown in sun or partial shade. The new variety is a *Hydrangea*, normally produced as an ornamental plant for containers or gardens.

2 Drawing Sheets

Latin name of the genus and species: *Hydrangea quercifolia.*

Variety denomination: 'BIV01'.

BACKGROUND OF THE INVENTION

The new *Hydrangea* cultivar is a product of chance discovery by the inventor in a personal garden in Ranburne, Ala.

The inventor identified an interesting seedling growing in a garden comprised of unnamed, unpatented *Hydrangea quercifolia* plants. The inventor observed this interesting plant over several years, noting the exceptionally dense flowerheads and later the bronze coloration of the Fall foliage.

Asexual reproduction of the new cultivar 'BIV01' by softwood cuttings was first performed during the May of 2012, at commercial nursery in Loxley, Ala. Subsequent propagation has shown that the unique features of this cultivar are stable and reproduced true to type in successive generations.

SUMMARY OF THE INVENTION

The cultivar 'BIV01' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BIV01' These characteristics in combination distinguish 'BIV01' as a new and distinct *Hydrangea* cultivar:

1. Exceptionally dense, inflorescence. Flowers are tightly packed together, producing a unique "spongey" texture.
2. Red-bronze Fall foliage.

3. Tolerance for both full sun and partial shade.
4. Long lasting inflorescence suitable for cut flowers.

PARENT COMPARISON

The inventor cannot accurately identify seed and pollen parents.

COMMERCIAL COMPARISON

'BIV01' are similar to plants of *Hydrangea quercifolia* 'Snow Queen', U.S. Plant Pat. No. 04,458, in most horticultural characteristics, however, plants of the new cultivar 'BIV01' differ in the following:

1. The new variety tolerates sun better than this comparator.
2. The new variety produces a much denser inflorescence than this comparator.
3. The new variety produces an inflorescence which is more round to slightly conical, this comparator produces a narrow conical inflorescence.

'BIV01' can be compared to the unpatented commercial variety *Hydrangea* 'Harmony'. These varieties are similar in most horticultural characteristics, however 'BIV01' differs in the following:

1. The new variety tolerates sun better than this comparator.
2. While this comparator produces a dense inflorescence, the new variety produces a denser inflorescence, with flowers packed even more tightly together.
3. Flowering stems of the new variety are stiffer and less prone to dropping or falling over under the weight of the flower.

BRIEF DESCRIPTION OF THE PHOTOGRAPHS

Figure 1:
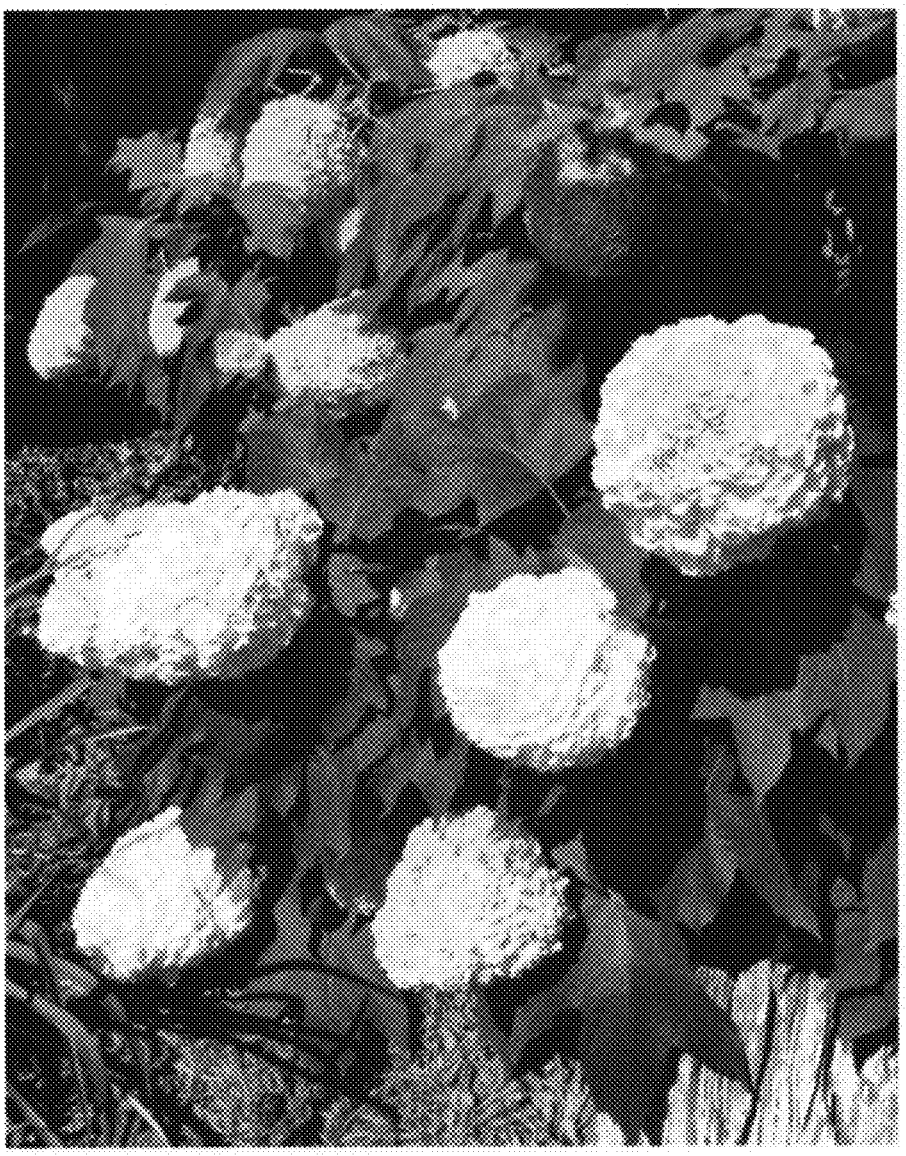

The accompanying photograph in FIG. 1 illustrates multiple inflorescence on a flowering plant of 'BIV01' grown in a outdoors in Loxley, Ala.

Figure 2:
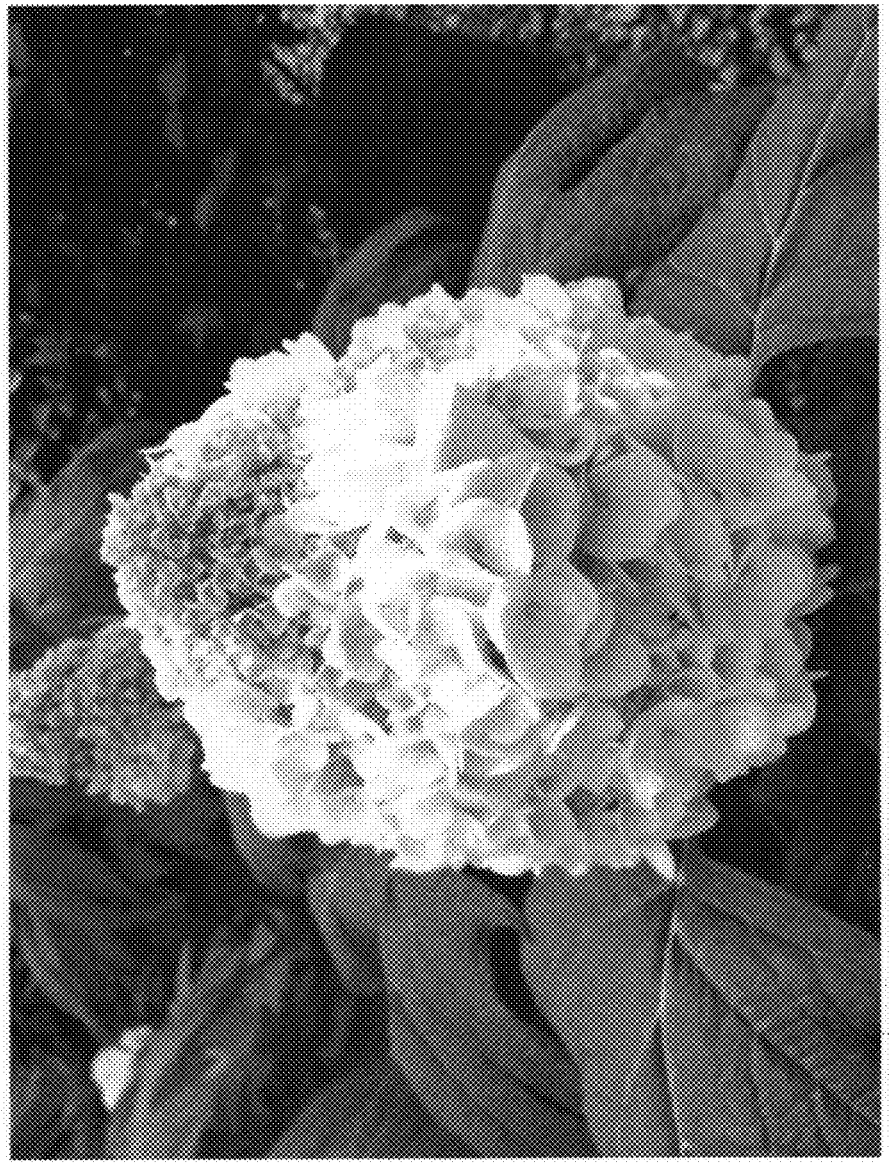

FIG. 2. illustrates in full color a typical inflorescence of 'BIV01'. Age of the plant photographed is approximately 2-3 years.

The photographs were taken using conventional techniques and although colors may appear different from actual colors due to light reflectance it is as accurate as possible by conventional photographic techniques.

DETAILED BOTANICAL DESCRIPTION

In the following description, color references are made to The 2007 Royal Horticultural Society Colour Chart except where general terms of ordinary dictionary significance are used. The following observations and measurements describe 'BIV01' plants outdoors, in Loxley, Ala. USA. The growing temperature ranged from approximately 18° C. to 27° C. daytime and 5° to 10° C. at night. Measurements and numerical values represent averages of typical plant types. Measurements were taken during August of 2016.

Botanical classification: *Hydrangea quercifolia* 'BIV01'.

PROPAGATION

Time to initiate roots: Approximately 18 days at approximately 27° C.

Time to produce a rooted young plant: Approximately 60 days at approximately 27° C.

Root description: Thick and fine, freely root branching and dense, fibrous. Color is white and brown, not accurately measured with an R.H.S. chart.

Propagation method: Softwood cuttings.

PLANT

Age of plant described: Approximately 2 years.

Pot size: 3 gallon.

Growth habit: Flowering, deciduous perennial shrub.

Overall plant shape: Broad V-shape.

Height: 50 cm.

Plant spread: 100 cm.

Growth rate: Good.

Plant vigor: Good.

Branching characteristics: Basal branching from a pinch.

Length of lateral branches: Average 25 to 35 cm.

Number of lateral branches: 4 to 6 main branches, each with 2 to 6 lateral branches, after pinching.

Diameter of lateral branches: 7 to 11 mm.

Lateral branch shape: Round.

Texture: Mature wood rough with thin, peeling bark. Immature branches densely puberulent.

Lateral branch strength: Moderate.

Internode length: Average range 3.0 to 7.0 cm.

Branch color: Immature: Near RHS Yellow-Green 152D, densely covered in hairs colored near Greyed-Orange 175B. Mature: Near RHS Greyed-Orange 175C, covered in bark colored Greyed-Green 197A.

Branch angle: 45 to 75°.

FOLIAGE

Leaf:

*Arrangement*.—Opposite.

*Average length*.—24 to 32 cm.

*Average width*.—12 to 16 cm.

*Shape of blade*.—Overall ovate, deeply lobed with 4 or more commonly 6 sinuses.

*Apex*.—Acute.

*Base*.—Rounded to truncate.

*Margin*.—Lobed. Uniformly serrate, 2 mm long serrations occurring 5 mm apart.

*Texture and appearance of top surface*.—Short hirsute, matte.

*Texture and appearance of bottom surface*.—Matte, mainly glabrous. Few hirsute hairs on veins.

*Color*.—Young foliage upper side: Near RHS Green 143A. Young foliage under side: Near RHS Green 138B. Mature foliage upper side: Near RHS Green 143A. Mature foliage under side: Near RHS Green 138B. Fall foliage upper side: Near RHS Greyed-Orange 175C flushed Greyed-Red 180A. Fall foliage under side: Near RHS Greyed-Orange 175D flushed Greyed-Red 180A.

*Venation*.—Type: Pinnate. Venation color upper side: Near RHS Greyed-Orange N170A. Venation color under side: Near RHS Yellow-Green 145B.

Petiole:

*Average length*.—7 to 9 cm.

*Diameter*.—5 mm.

*Color*.—Upper side: Near RHS Greyed-Yellow 161B. Under side: Near RHS Yellow-Green 145B.

*Texture upper side*.—Pubescent.

*Texture under side*.—Pubescent.

FLOWER

Bloom period:

*Natural season*.—Early Summer until Fall.

Inflorescence:

*Arrangement*.—Terminal corymb. Very dense.

*Commercial type*.—Mophead.

*Infloresence shape*.—Globular to somewhat conical.

*Panicle height*.—15 to 20 cm.

*Panicle diameter*.—15-20 cm.

*Panicle shape*.—

*Quantity of flowers per inflorescence*.—Fertile flowers not observed to date. Sterile Flowers, 250 to 450 approximate average.

*Persistent or self-cleaning*.—Persistent.

*Fragrance*.—None.

*Vase life*.—2 to 3 weeks.

Sterile flower:

*Bud shape*.—Obovate.

*Bud length*.—4.0 mm.

*Bud diameter*.—5.0 mm.

*Bud color*.—Near RHS Yellow-Green 145A.

*Flower aspect*.—Upright and outward.

*Flower shape*.—Cruciform.

*Flower diameter*.—Average range 20 to 25 mm.

*Flower depth*.—10 mm.

*Aspect*.—Upwardly cupped.

Sterile flower sepals:

*Petal arrangement*.—Cruciform.

*Petal number*.—4.

*Length of petal*.—Approximately 11 to 15 mm.

*Width of petal*.—Approximately 10 to 12 mm.

*Angel of attachment/aspect*.—Petals angled upward approximately 45° from point of attachment. Petals upwardly cupped.

*Apex*.—Rounded.

*Shape of petal*.—Obovate.

*Petal margin*.—Entire.

*Petal base*.—Obtuse.

*Petal texture*.—Smooth, upper and under sides.

*Color*.—Upper surface at first opening: Near RHS Yellow-Green 145A, blotched Green 143C. Upper surface at maturity: Near RHS White 155A. Under surface at first opening: Near RHS Yellow-Green 145C, blotched Yellow-Green 143A. Under surface at maturity: Near RHS White 155A. Color when fading: Upper and lower surfaces: Near RHS Yellow-Green 145A.

Sterile flower petal: Highly reduced and malformed structure. Less than 1 mm, colored near Yellow-Green 145A.

Sterile flower pedicel:

*Length*.—10 to 12 mm.

*Diameter*.—1 mm.

*Angle*.—Upright and outward.

*Strength*.—Flexible, not prone to breakage.

*Texture*.—Smooth.

*Color*.—Near RHS Yellow-Green 145B.

Fertile flower: Not observed to date.

REPRODUCTIVE ORGANS

Sterile flower: All reproductive parts irregular and malformed, reduced to less than 1 mm or not present.

OTHER CHARACTERISTICS

Disease resistance: Neither resistance nor susceptibility to diseases or pests has been observed in this variety.

Temperature tolerance: USDA Zones 5 through 9. No tolerance for drought.

Fruit/seed production: Seed production not observed to date.

What is claimed is:

1. A new and distinct cultivar of *Hydrangea* plant named 'BIV01' as herein illustrated and described.

* * * * *